(12) United States Patent
Bilenski et al.

(10) Patent No.: US 6,979,340 B2
(45) Date of Patent: Dec. 27, 2005

(54) SINGLE USE, SELF-CONTAINED TWIST RESISTANT SURGICAL KNIFE

(76) Inventors: Edward Bilenski, 10 Manning Ave., Butler, NJ (US) 07405; Noel C. Cobb, 77 Cobb Rd., Mountain Lakes, NJ (US) 07046

( * ) Notice: Subject to any disclaimer, the term of this patent is extended or adjusted under 35 U.S.C. 154(b) by 67 days.

(21) Appl. No.: 10/822,243

(22) Filed: Apr. 9, 2004

(65) Prior Publication Data

US 2005/0228421 A1    Oct. 13, 2005

(51) Int. Cl.[7] .............................................. A61B 17/32
(52) U.S. Cl. ..................................................... 606/167
(58) Field of Search ............................... 606/167–170; 30/49, 351, 357, 152, 294

(56) References Cited

U.S. PATENT DOCUMENTS

| 845,792 A | 3/1907 | Jenkins | |
| 1,424,221 A | 8/1922 | Trumpeter | |
| 2,512,237 A | 6/1950 | Mravik | 30/151 |
| 3,906,626 A | 9/1975 | Riuli | 30/162 |
| 5,330,492 A | 7/1994 | Haugen | 606/167 |
| 5,417,704 A | 5/1995 | Wonderley | 606/167 |
| 5,556,409 A | 9/1996 | Haining | 606/181 |
| 5,741,288 A | 4/1998 | Rife | 606/181 |
| 5,779,724 A | 7/1998 | Werner | 606/167 |
| 5,908,432 A | 6/1999 | Pan | 606/167 |
| 6,022,364 A | 2/2000 | Flumene et al. | 606/166 |

*Primary Examiner*—Tan-Uyen T. Ho
(74) *Attorney, Agent, or Firm*—Ernest D. Buff & Associates, LLC; Ernest D. Buff; Theodore J. Pierson

(57) ABSTRACT

A single use self-contained surgical knife provides twist stability and lateral support for the knife blade. Turning a knurled ring member within the containment casing retracts the knife blade into the containment casing. Retraction of the blade is permanent; once retracted, subsequent usage of the knife blade is prevented. A substantial safety margin is provided, in that injuries occasioned by the retraction process are virtually eliminated. The knife blade remains forever in the retracted condition, preventing spread of blood borne infections such as AIDS, Hepatitis and the like, that might otherwise result from subsequent usage of the knife blade.

6 Claims, 2 Drawing Sheets

Fig. 1.
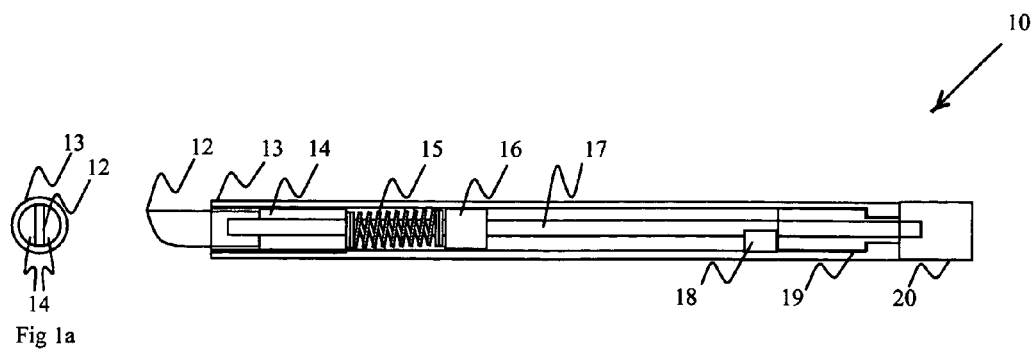
Fig 1a
Fig. 2.
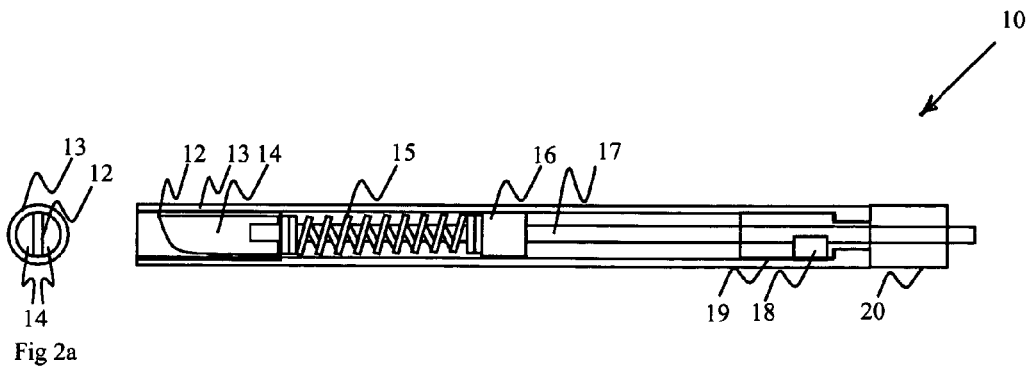
Fig 2a

SINGLE USE, SELF-CONTAINED TWIST RESISTANT SURGICAL KNIFE

BACKGROUND OF THE INVENTION

1. Field of the Invention

This invention relates to knives used in surgical procedures; and more particularly to a single use, self-contained, twist resistant surgical knife having a blade locking and retraction mechanism that can be actuated with a one-hand following knife use to prevent its reuse and impede transmission of blood borne diseases such as AIDS.

2. Description of the Prior Art

Retractable knifes have heretofore been designed which allow extension of the knife blade and retraction of the blade into a handle. U.S. Pat. No. 845,792 to Jenkins, discloses a knife which is retractable within the handle by pushing against a spring, and is locked in place using a pin. The knife is released from the handle by the compressive forces of the spring when the pin is released. Such a knife does not prevent subsequent usage, and the blade is not securely held to prevent lateral displacements and twisting. U.S. Pat. No. 1,424,221 to Trumpeter discloses an ice pick, which is retractable into the handle against a spring and can be locked in the ice pick point exposed or retracted within the handle. A tubular nut secures the pick point in a hidden condition, within the handle, or an exposed condition, outside the handle. Owing to its mechanism, the ice pick does not prevent subsequent usage, and its blade is not securely held to prevent lateral displacements and twisting. U.S. Pat. No. 2,512,237 to Mravik discloses a pocket implement wherein a blade is retracted within a flattened cylindrical sheath enclosure to facilitate carrying the implement in a pocket or handbag. The blade is exposed by pushing the sheath into the handle against a spring, and is held in place by a catching mechanism. The flattened cylindrical sheath provides very limited support for the blade, allowing lateral movement and twisting of the blade. Such a mechanism permits multiple use of the blade. U.S. Pat. No. 3,906,626 to Riuli discloses a unitary disposable surgical scalpel. The scalpel is supplied with the blade exposed. After use it is pushed into a sheath and permanently locked, after which the scalpel is disposed. Once locked, the sheath cannot be removed without completely destroying the sheath. The surgeon essentially holds the sheath to use the knife. A loose fit between the sheath and the retractable blade allows twisting of the blade, preventing precise use of the surgical blade. U.S. Pat. No. 5,330,492 to Haugen discloses a safety scalpel attached to the forward end of a handle. A spring biased retractable sheath is positioned within the handle. Depressing a single button, which pushes the sleeve against the blade, actuates the blade retraction action. The knife can be reused many times and can be withdrawn from the sleeve. It is therefore not a single use device. The blade is handled by using the sleeve, causing lateral and twist instability of the blade during use. U.S. Pat. No. 5,417,704 to Wonderley discloses a disposable surgical scalpel with a U shaped plastic safety guard. The blade is carried on one end of the handle and a plastic safety guard is slid cover over the blade in a protective position or moved away to expose the blade. Displacing the guard beyond a wedge permanently locks the knife. This patented device is a disposable surgical scalpel with a U shaped guard that can be positioned in one of three positions. The U shaped guard can be moved rear-wise to expose the blade, displaced forward to temporarily protect the blade and displaced all the way forward to permanently lock the scalpel. Due to the existence of the intermediate position, the scalpel is not a single use self-contained surgical knife. The U shaped guard has to be slid over a wedge to permanently lock the wedge. Such sliding action may require substantial force, raising the possibility of knife slippage and injury to the surgeon. Since the knife is handled using the guard, the sloppiness between the blade and the U shaped guard causes lateral and twisting displacements of the blade. U.S. Pat. No. 5,556,409 to Haining discloses a disposable scalpel with a retractable blade. The blade can be positioned in an intermediate retracted position for shipping; a fully exposed position for use; and a permanently retracted position for safe disposal. The blade handle has a chamber with projections and a blade carrier having a flexible member which engages with the projections to secure the blade in these three positions. Pressing a tap with the finger controls the blade motion. The tap is sealed once the blade is retracted. This disposable surgical scalpel can move the blade in one of three positions. The blade is moved by pressing on a tap with a finger and this allows sliding if a blade carrier is inside the chamber in the handle. Since the carrier has to slide in the chamber over the projections by finger pressure, there is a degree of loose tolerance between the width of the blade carrier and the width of the chamber, allowing twisting motion of the blade. This loose tolerance prevents precise cutting action by the surgeon. Also this device can be used many times by sliding between the use position and the shipping position, preventing its applicability as a single use device. Also the sliding force needed to lock the blade may accidentally cause injury to the surgeon due to slippage. U.S. Pat. No. 5,741,288 to Rife discloses a rearmable single user safety finger stick device having a reset for multiple use by a single patient. A lancet is extended beyond a hole in the body of the device upon actuation to create a small incision to extract a drop of blood for self-test. Upon arming, the lancet carrier is withdrawn storing energy in a spring in the body of the device. When the lancet is released by pressing a button, the lancet extends outward through a hole in the body over which the user's finger is placed to create the incision. This device is a lancet and is not a single use self-contained surgical knife. U.S. Pat. No. 5,779,724 to Wemer discloses a retractable surgical knife. The device is similar to a ball pen in construction wherein the blade is pushed out by pressing a latch mechanism and retracted by again by pushing on the latch mechanism. The blade is carried in a central carrier and is prevented from falling out. A new scalpel blade can be attached into the device as shown in col. 9 lines 40–50. The blade support assembly is pushed forward to expose the blade and the push button is pushed transversely to retract the blade. Such a device is not a single use, self-contained surgical knife. It is not stable and presents problems during operation, since the blade tends to move laterally and twists due to loose tolerances with which the blade is held in the device containment. U.S. Pat. No. 5,908,432 to Pan discloses a scalpel having a retractable blade. The blade is retained in a blade holder and is slidable within a channel in the distal section of the handle. Such sliding action essentially guards the blade from accidental contact. The retraction function is actuated when the surgeon pushes a spring-loaded button. Such a blade is an actuated, retractable blade that swings into a channel in the handle. This mechanism does not permit the surgical knife to provide a single use, self-contained function. Moreover, loose tolerances between the blade and the handle cause lateral and twist instability of the blade during surgical use. U.S. Pat. No. 6,022,364 to Flumene et al. discloses a disposable surgical safety scalpel. The blade and blade support act as a slider in a shell, and are guided by the shell walls while extending into the in-use position or retracting into the shell. When the blade is extended, the spring in the handle is stretched to produce tension against a pin. During actuation of the pin, tension in the spring is released retracting the blade into the sheath. FIGS. 2 and 4 of U.S. Pat. No. 6,022,364 indicate the position of the spring in the blade retracted and blade exposed conditions. This is not a single use self-contained surgical knife, since the blade can be retracted and brought back into operating position repeatedly. Due to the large area over which the blade holder slides against the sides of the shell, a large clearance must be provided to facilitate the extension and retraction of the blade. As a result, the blade is not held rigidly, and it is difficult for the surgeon to produce precise incisions when using the handle to hold the knife.

Knifes and sharp implements which can be retracted have been extensively disclosed by prior art workers. Disclosures exist involving numerous mechanisms for retraction of surgical knives. No disclosure exists concerning a single use self-contained surgical knife. Instead, each of the mechanisms disclosed permits reuse in one form or other Moreover, there is a fundamental conflict between knife retractability and knife twist stability. Knife retractability using spring mechanisms requires that the knife be easily moved by spring tension. The surgeon typically uses a handle to hold the knife, causing instability of the blade due to lateral displacements and twisting of the blade. This twisting motion prevents the surgeon from producing accurate incisions. For this reason, retractable surgical knifes have heretofore not enjoyed widespread use in surgery.

Key factors for improved knife stability require that the surgical blade be supported in all directions. The support mechanism must be such that the blade is still withdrawn using a small spring tension. Previous attempts to provide retraction capability have not produced a surgical knife having this functionality.

As a consequence remains a need in the art for a single use self-contained surgical knife which provides lateral and twist stability. The retraction process of the blade must function reliably, and be actuated by internal mechanisms of the device that are triggered when the surgeon activates or rotates a single knob with one hand. The retraction of the blade must be accomplished without use of excessive force and must completely prevent reuse of the blade, in order to prevent blood borne infections from being transmitted. This need has heretofore not been met by retractable surgical knives previously proposed by prior art workers.

SUMMARY OF THE INVENTION

The present invention provides a single use self-contained surgical knife having a knife blade that is fully supported against twisting motion by faces of slot. The blade is attached to a shaft that is supported on two bushings to provide lateral stability; and travels at all times between two adjacent faces, forming a slot. The blade is supplied to the surgeon in an armed 'in-use' condition that is created by compression of a spring. This position is held by a rectangular lug resting against a knurled ring member, held loosely against the casing of the single use self-contained surgical knife. The misalignment between the rectangular lug and the rectangular opening in the knurled ring member locks the knife in the extended 'in-use' position. When the surgeon decides to throw away the knife, he rotates the knurled ring member, thus aligning the rectangular lug with the rectangular opening in the knurled ring. This alignment condition forces the compression spring to retract the shaft that carries the knife blade. Advantageously, the rotation step can be readily accomplished by the surgeon in a one-hand operation. After retraction, the rectangular lug and the rectangular opening are separated from each other due to expansion of the spring. There exists no mechanism by which the knife blade can be extended, so that the knife is not reusable. At all times the knife shaft is fully supported by the bushings and the slot faces support the blade from twisting during use. A low friction coefficient between the knife blade and adjacent faces of the slot is achieved by use of polymeric materials such as PTFE, HDPE and the like. Constructing the slot with these materials facilitates easy retraction of the blade into the casing by releasing the spring compression. The sliding surfaces of the knurled component ring, which rub against the rectangular lug, may be made from PTFE, HDPE and other low friction polymeric materials. This construction facilitates easy rotation of the knurled ring by the surgeon using a single hand.

BRIEF DESCRIPTION OF DRAWINGS

The invention will be more fully understood and further advantages will become apparent when reference is had to the following detailed description and the accompanying drawings, in which:

FIG. 1 is a perspective front and side view of a single use self-contained surgical knife in the in-use position, with support being provided for lateral displacement and twisting of the blade during use;

FIG. 2 is a perspective front and side view of a single use self-contained surgical knife in the blade retracted condition, with support provided for lateral displacement and twisting of the blade.

DESCRIPTION OF THE PREFERRED EMBODIMENTS

Figure 3:
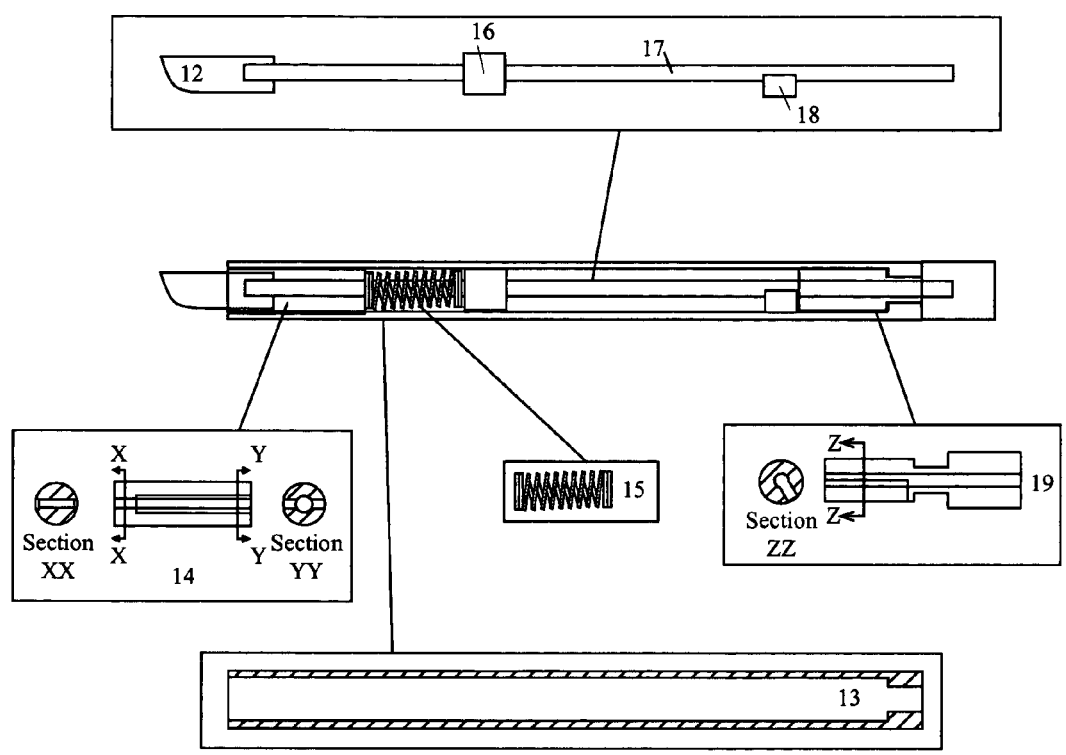
FIG. 3 is an exploded view of a single use self-contained surgical knife in the in-use condition, showing geometrical details of various components in the single use self-contained surgical knife.

As used herein, the term "single use self-contained surgical knife" means surgical knife provided in the 'in-use' mode, which is sterile and ready for use. That is to say, no extension of the knife is required; since the knife blade is first presented in the extended condition. When the surgeon has finished using the knife and is ready to discard it, a knurled ring member is turned, triggering retraction of the knife blade into the casing. Retraction, once triggered, is permanent. A new blade cannot be inserted and the used blade is totally contained within the casing, from which it cannot be removed without destroying the device. The term 'twist resistant' means that the blade in the extended condition is completely supported in all three directions and the blade does not have any unexpected motion. In addition, incision loads applied to the blade do not cause the thin blade to twist or otherwise result in angular, unwanted incisions.

Key features involved in the design and application of a single use self-contained surgical blade include 1) means for providing support for the knife in all three directions and providing blade twist support using parallel faces of slots which encase the blade; 2) means for loading a compression spring when the blade is extended beyond the containment casing in the 'in-use' position, so that the knife blade will go back into the containment casing automatically due to spring extension from the compressed state; 3) means for achieving on a one time basis a blade locking condition, in which the blade is locked in the 'in-use' position by use of a rectangular lug and a corresponding opening in the knurled ring member; 4) means for releasing the knife blade by turning a knurled ring member connected to the rectangular opening to thereby release the lug and cause the spring to push the knife blade back into the containment casing; and 5) means for effecting complete separation of the rectangular lug and the rectangular opening so that it is impossible to extend the knife blade into in-use position. Low friction at the slot support faces and bushings is provided by constructing these components of low friction polymers such as PTFE or HDPE.

Referring to FIG. 1 there is shown at 10 the front and side view of a single use self-contained surgical knife assembly. The knife 12, as shown, is in the 'in-use' position, and is shipped to the surgeon in that condition, ready for use. The containment casing 13 is depicted as being transparent for illustration purposes so that the interior components can be viewed. The knife blade 1 is shown outside the containment. A pair of parallel slots in the support member 14 restrain the blade from twisting motion and the knife shaft is free to slide within this support member 14 by the bushings. The containment casing structure 13 completely encloses the single use self-contained surgical knife device, but for one opening provided for knife extension. The bushings in support member 14, which also supports the central knife shaft, 17, holds the knife with lateral support. The support member 14 is permanently attached to the containment casing structure 13 and the central knife shaft 17 freely moves through the support member 14 bushings. A cylindrical lug 16 is permanently attached to the central knife shaft 17 and is pressed against one end of the compression spring 15. The other end of the compression spring 15 rests against the support member 14, which is attached permanently to the containment casing 13. The central knife shaft also carries a rectangular lug 18. The compression in the spring 15 is maintained by the rectangular lug 18 being out of alignment with a rectangular opening in the knurled ring member 20. The ring member 19, which is knurled at its outer surface 20, is attached to the containment casing. Ring member 19 is provided with a central hole for the passage of the central knife shaft 17, and is adapted to be rotated axially over the containment casing 13. When the spring 15 is in the compressed state, the rectangular lug 18 rests on the face of the ring member 19. In this condition, the rectangular opening in the ring member is misaligned with respect to the position of rectangular lug 18, which is attached to the central knife shaft 17. After using the knife, the surgeon turns the knurled ring 20 to rotate the member 19, thereby aligning the lug 18 with the rectangular opening in the ring member 19. Alignment of lug 18 with the rectangular opening in ring member 19 operates to release the spring compression. The knife blade is thereby withdrawn permanently into the containment casing structure. FIG. 1a is a side view of the surgical knife in the 'in-use' position. The knife 12 is supported by the parallel slots in the support member 14, which is permanently attached to the containment casing 13.

Referring to FIG. 2, there is shown at 10 a front and side view of the knife in the retracted position after the surgeon has turned the knurled ring member 20, allowing the rectangular lug 18 to pass through the rectangular opening in the ring member 19. Now the compression spring 15 is in the natural relaxed state and is no longer under compression. The spring is still in between the support member 14 and the cylindrical lug 16 attached to the central knife shaft 17. The shaft and the knife have been pushed back into the containment casing by the release of spring compression. There is no way the rectangular lug 18 can be inserted back into the rectangular opening in the knurled ring member 19 to extend the knife into the 'in-use' position, since the ring member rectangular opening and rectangular lug are no longer aligned. Extending the knife requires the spring 15 to be compressed. At the same time, the rectangular opening in the ring member 19 becomes misaligned with respect to the rectangular lug 18 attached to the central knife shaft 17. This is not possible since the central knife shaft does not extend beyond the knurled ring member to create required compression of the spring. FIG. 2a is a side view of the surgical knife in the retracted position. The knife 12 is contained within the parallel slots in the support member 14, which is permanently attached to the containment casing 13.

Referring to FIG. 3, there is shown an exploded view of a single use self-contained surgical knife in the in-use condition. Specifically shown are geometrical details involving various components of the single use self-contained surgical knife. The containment casing 13 is essentially a tube with one end with a reduced diameter opening for accepting the knurled ring member. The central knife shaft 17 carries the blade knife 12, cylindrical lug 16 and rectangular lug 18. Details of support member 14 are shown rotated 90 degrees. The left side shown at cross section XX allows the blade to pass through easily providing lateral support to the blade as well as twist stability. The bushings in the support member 14 provide lateral support to the central knife shaft. The right side of the support member 14 allows both the blade and the central shaft 17 to pass through. The blade with the shaft attached to it can only move forward until the shaft reaches the end of its opening in the support member. The right side of the support member acts as one resting end of the compression spring 15 and the other resting end is the cylindrical lug 16 on the central knife shaft assembly. The knurled ring member 19 fits inside the containment casing 13 and is rotatable. It has a central hole for the central knife shaft assembly 17 to pass through freely. It also has a slot milled in it as a rectangular opening as shown in the cross section of the left side of the knurled ring member at ZZ. When the knife is extended the rectangular opening is misaligned with respect to the rectangular lug 18 in the central knife shaft assembly so that the spring 15 is held in compression.

Turning the knurled ring member aligns the rectangular opening in the ring member with the rectangular lug in the central knife shaft and releases the compression in the spring propelling the central knife shaft assembly, whereby the blade becomes permanently retracted into the containment casing 13.

During manufacture of the single use surgical knife a special tool is used to push the central knife shaft into the extended condition. The tool compresses the spring and at the same time aligns the rectangular opening of the knurled ring element and the rectangular lug in the central shaft assembly and immediately misaligns the knurled ring member to maintain compression in the spring and extend the knife blade. The knife is supplied to the surgeon with the knife blade extended. After a single use, the surgeon turns the knurled ring member to retract the knife blade permanently into the containment casing.

Having thus described the invention in rather full detail, it will be understood that such detail need not be strictly adhered to, but that various changes and modifications may suggest themselves to one skilled in the art, all falling within the scope of the invention as defined by the subjoined claims. For example a different capturing and retracting mechanism may be used to retain the knife blade in the 'in-use' position, and a different release mechanism may be used or a different manufacturing sequence may be employed.

What is claimed is:

1. A single use self-contained surgical knife having a single blade, comprising:
   a. containment means for housing said surgical knife blade;
   b. stabilization means having at least a pair of slot faces for preventing twisting of said blade;
   c. retraction means for exerting spring tension on said knife blade to move said blade into said containment means;
   d. locking means comprising a rectangular lug misaligned to a rectangular opening in a knurled ring member, for locking said knife blade in an 'in-use' position;

wherein a user turns said knurled ring member after using said surgical knife in order to release the rectangular lug and retract the knife blade permanently into the said containment casing.

2. A single use self-contained surgical knife as recited by claim 1, wherein said slot faces are formed in a slot block, and said slot block is attached to the containment casing.

3. A single use, self-contained surgical knife as recited by claim 2, wherein said slot faces are coated with a low friction material.

4. A single use, self-contained surgical knife, as recited by claim 2, wherein said slot block is fabricated from PTFE, HDPE or other low friction material.

5. A single use, self-contained surgical knife, as recited by claim 1, wherein said knurled ring member is coated with a low friction coating for easy release of said rectangular lug.

6. A process for making a single use self-contained surgical knife, comprising the steps of:
   a. assembling together a plurality of components to form a central knife shaft assembly of said surgical knife, said components including:
      (i) a central shaft;
      (ii) a welded knife blade;
      (iii) a welded cylindrical lug; and
      (v) a welded rectangular lug;
   b. assembling component parts of a two part containment casing structure having a containment member and a support member capable of providing lateral and twist support for said knife blade and said central knife shaft assembly;
   c. inserting said central shaft assembly into said support member;
   d. inserting a compression spring to rest on said support member;
   e. inserting a knurled ring member aligning a rectangular opening with a rectangular lug of said central knife shaft assembly;
   f. compressing said compression spring against said cylindrical lug; and
   g. turning said knurled ring member to misalign said opening with said lug.

* * * * *